United States Patent [19]

Yoshida

[11] 4,360,932
[45] Nov. 30, 1982

[54] URINATION DISPOSAL BAG

[76] Inventor: Toshiya Yoshida, 21-9 Tamagawa 1-chome, Ohta-ku, Tokyo, Japan

[21] Appl. No.: 246,634

[22] Filed: Mar. 23, 1981

[30] Foreign Application Priority Data

Jun. 19, 1980 [JP] Japan ............................. 55-84863[U]

[51] Int. Cl.³ ............................................. A47K 11/12
[52] U.S. Cl. ..................................................... 4/144.2
[58] Field of Search ..................................... 4/450–452, 4/454, 457, 144.1–144.3; 128/275, 295, 762, 767

[56] References Cited

U.S. PATENT DOCUMENTS

| 2,445,220 | 7/1948 | Isaacson | 128/295 |
| 2,863,457 | 12/1958 | Barach | 128/295 |
| 3,295,145 | 1/1967 | Erickson | 4/144.3 |
| 3,613,123 | 10/1971 | Langstrom | 4/144.1 X |
| 4,197,849 | 4/1980 | Bostick | 4/144.3 X |

Primary Examiner—Charles E. Phillips
Attorney, Agent, or Firm—George B. Oujevolk

[57] ABSTRACT

A disposable urination bag having a liquid impermeable exterior having a slit which is above the tangent line of two rolls of absorbant material, thus forming a cavity to accept the male genital organ.

1 Claim, 2 Drawing Figures

U.S. Patent   Nov. 30, 1982   4,360,932
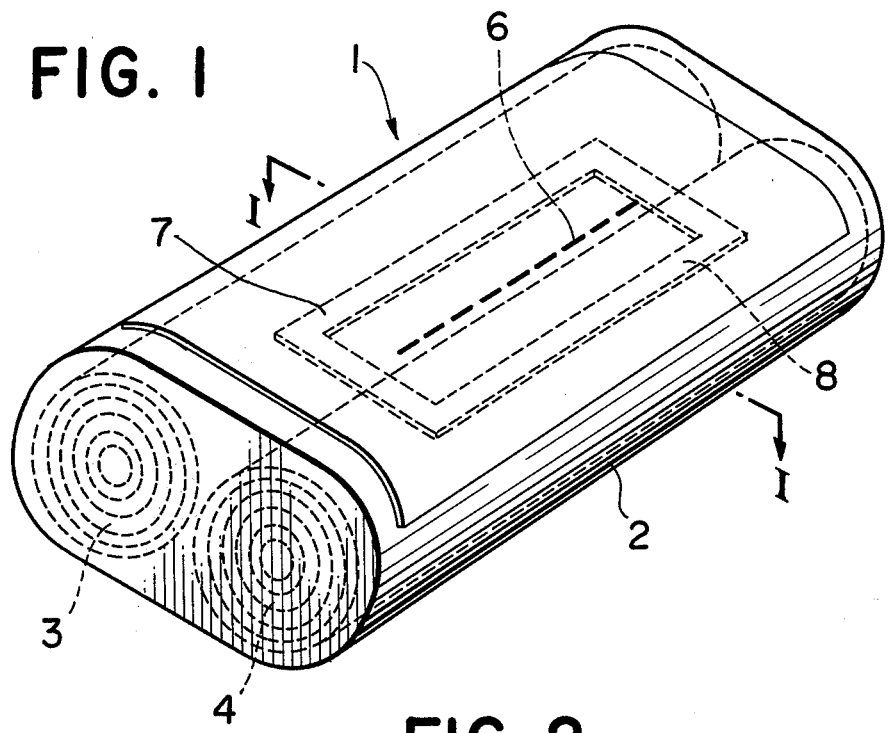
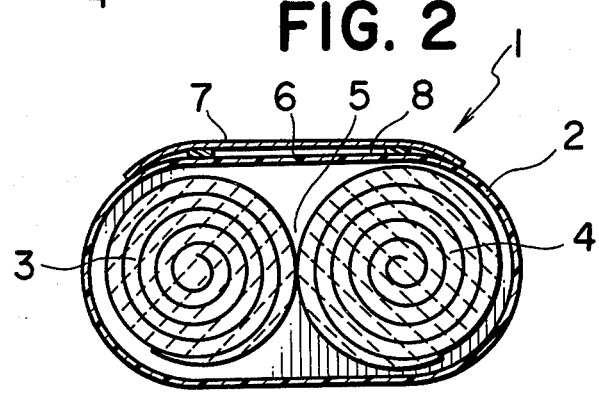

URINATION DISPOSAL BAG

This invention relates to a urination disposal bag adapted for use when, for example, an old man confined to his bed or a sick person and so on disposes of his urination.

There is a tendency that the number of persons who are confined to their ill bed in hospitals or at homes increases along with a rise of an old age population or an increment of traffic accident injuries; and in addition, as medical science progresses there may be many peoples who are scarcely saved from death in an accident and require care an nursing, having troubles in their members and being not able to lead everyday life for themselves.

Urinals or urine bags are known as appliances for receiving urine when a sick person confined to his bed in hospital or at home urinates while lying in his bed. However, urinals are generally put on the floor below the bed and because of their troublesome of handling it is difficult for an invalid in bed to use them.

Also, when a sick person uses a paper diaper in bed it may give a feeling of a certain unfitness to the person using it, and moreover, it has such drawbacks that it may cause an injury to a person at his private parts and the portions around them due to the stuffiness of the paper diaper since paper diapers are generally of a square shape having a substantial dimension and are essentially to be used applied at the crotch for incontinence and the like and are not destined for receiving urine.

Moreover, when a nurse uses an appliance such as mentioned above, it is impossible for her to dispose of the nursing at her pace; that is to say, with regard to feces, while it may be approximately once or so a day to dispose of, in case of urine, it may be several times and, frequently, some dozen times a day to dispose of, and in particular, it often occurs to dispose of urine in the night. In case of hospitals in countries having a number of nurses and various necessary equipments or facilities, urine disposal in the nighttime such as mentioned above may readily be effected on request of patients, but the actual circumstances are that for many peoples it is unable to be in hospital for a long time in which a sufficient number of nurses are employed and many facilities are provided.

The actual situation is therefore that even though hospitalized many patients are being attended to by their family member or by a nurse employed for a heavy expense, or being at home back from hospital, by one or more of their family members serving as home attendant. Particularly, when there is a sick person in a family who is to be attended to by family members, the attendant members would suffer from incapability of taking enough sleep due to repeated disposals of urine for the sick person in the nighttime, and after a series of such heavy days of nursing they would often become sick so that they could not continue nursing further.

Moreover, sick persons are often too nervous not to wake up their attendant(s) in the nighttime and will not take much water in order to avoid possible repeated urinations, thereby often resulting in a dehydrated condition of the sick persons to thus worsen their condition.

This invention has been made under such circumstances as described above and therefore aims at providing simple urination disposal bags enabling an attendant to easily dispose at his pace of the urination of, so to speak, a sick person generally confined to sick bed who has in particular disabled hands and feet and cannot therefore dispose of his urination, and also aims at giving an invalid an entire satisfaction as to his urination volition.

The accompanying drawings show one preferred embodiment of the present invention, wherein:

FIG. 1 is a perspective view showing generally the invention; and

FIG. 2 is a sectional view taken along the line I—I of FIG. 1.

The invention will now be described in detail hereunder with reference to the accompanying drawings, in which 1 shows a urination disposal bag (hereinafter referred to as "a disposal bag") totally.

The disposal bag 1 is provided with a bag body 2 made from impermeable material such as, for example, vinyl and the like. Within the bag body 2, there are provided, in the case of this embodiment, absorption bodies 3, 4 that are made from towel rolled up in a volution form. Absorption bodies 3, 4 should not be limited to towel, but may be of any other equally functionable material such as for example cotton, paper and the like. Also, they may be in any other form than a rolled up form. However, important in particular is that they should consist of two bodies.

An insertion slit 6 is provided on the upper surface of the bag body 2 corresponsive with the boundary portion 5 of the absorption bodies 3 and 4. In order to prevent the insertion slit 6 from tearing, there may be provided around the slit 6 a frame 8 formed by bonding vinyl tape and the like. Furthermore, for covering over the insertion slit 6, any soft material such as for example table napkin, toilet-paper, tissue paper and the like is adhered to the upper surface of the bag body 2.

Thus, in using a disposal bag of the present invention, the user (male) inserts his genital organ into the insertion slit 6 so that the genital organ may softly be caught between the two absorption bodies 3, 4, and in that condition the user can urinate at will and the urine thus urinated will be absorbed by the absorption bodies 3, 4.

As the absorption bodies 3, 4 comprise two parts, it is easy for a sick person to insert his genital organ between them and, furthermore, the absorption volumetric capacity of the absorption bodies 3, 4 is sufficiently big so that a substantial amount of urine may be absorbed therein. The disposal bag 1 may be made disposable after each onetime use.

The present invention being comprised of as described above, a sick person who has disabled hands and/or feet and is to often urinate in the nighttime or an invalid who tends to often urinate in the daytime can prior insert his genital organ into the insertion slit of the disposal bag through the assistance of an attendant or by himself and can urinate into the bag at will so that the handling of the bag is very simple and convenient.

Also, the nurse or attendant will be able to enjoy a good sleep without being aroused out of her (or his) sleep by the sick person or invalid in the nighttime so the disposal bag of this invention is optimum for a long term nursing. Furthermore, since the absorption bodies are totally contained in the bag there is no fear for a handler of having his hands stained, and in addition, as the absorption bodies consist of two bodies it will be possible for a user to insert his genital organ smoothly into the bag.

Additionally, as a thin and soft sheet of paper is adhered to the surface of the disposal bag, no steaming will occur in the region even where the bag directly may touch the skin so that no dermatitis may occur in the body.

I claim:

1. A substantially box-shaped urination disposal bag, comprising in combination: a liquid impermeable bag body having a defined upper surface; a rectangular frame at said upper surface with a defined insertion slit within said frame; a soft covering around said slit; a plurality of elongated rolled-up absorption bodies extending across said bag horizontally so that the longitudinal axis of said bodies is under and parallel to said slit, said bodies substantially filling up said box-shaped bag so as to give said bag the substantially rectangular box-like appearance, said bodies forming two tangent rows of substantially the same length, with the line of contact of said tangent rolls being under said slit and cooperating to form an area of near triangular cross section under said slit to accept a genital organ inserted through said slit; and, a cover disposed between said frame and said bag.

* * * * *